United States Patent [19]

Snyder et al.

[11] Patent Number: 4,847,199
[45] Date of Patent: Jul. 11, 1989

[54] AGGLUTINATION IMMUNOASSAY AND KIT FOR DETERMINATION OF A MULTIVALENT IMMUNE SPECIES USING A BUFFERED SALT WASH SOLUTION

[75] Inventors: Brian A. Snyder, Rochester; Robert T. Belly, Ithaca, both of N.Y.

[73] Assignee: Eastman Kodak Company, Rochester, N.Y.

[21] Appl. No.: 19,850

[22] Filed: Feb. 27, 1987

[51] Int. Cl.$^4$ .......................... C12M 1/12; C12Q 1/04; C12Q 1/14

[52] U.S. Cl. .......................... 435/36; 422/61; 422/73; 422/101; 422/102; 435/7; 435/291; 435/810; 436/510; 436/511; 436/532; 436/533; 436/808; 436/810; 436/811; 436/814; 436/818

[58] Field of Search .......... 435/7, 36, 810, 291; 422/61, 73, 101–102; 436/510, 511, 532, 533, 808, 810, 814, 811, 818

[56] References Cited

U.S. PATENT DOCUMENTS

| | | | |
|---|---|---|---|
| 3,853,987 | 12/1974 | Dreyer | 424/1 |
| 4,039,652 | 8/1977 | Adams et al. | 424/1 |
| 4,108,972 | 8/1978 | Dreyer | 424/1 |
| 4,200,690 | 4/1980 | Root et al. | 435/7 |
| 4,407,943 | 10/1983 | Cole et al. | 435/7 |
| 4,419,453 | 12/1983 | Dorman et al. | 436/534 |
| 4,459,361 | 7/1984 | Gefter | 436/523 |
| 4,478,946 | 10/1984 | Van der Merwe et al. | 436/518 |
| 4,552,839 | 11/1985 | Gould et al. | 435/7 |
| 4,591,571 | 5/1986 | Kuboyama et al. | 436/533 |
| 4,618,576 | 10/1986 | Rosenstein et al. | 435/7 |
| 4,636,479 | 1/1987 | Martin et al. | 436/520 X |
| 4,673,639 | 6/1987 | Slifkin | 435/36 |
| 4,707,450 | 11/1987 | Nason | 422/61 X |

FOREIGN PATENT DOCUMENTS 0150567 6/1985 European Pat. Off. .
0174195 3/1986 European Pat. Off. .

OTHER PUBLICATIONS

Slifkin et al, *J. Clin. Microbiol*, 15 (1), pp. 187–198, 1982.
SIGMA Chemical Company Catalog (price list), Feb. 1984, p. 721.
Slifkin et al, *J. Clin. Microbiol*, 20(1), pp. 12–14, 1984.

Primary Examiner—Barry S. Richman
Assistant Examiner—Jill Johnston
Attorney, Agent, or Firm—J. Lanny Tucker

[57] ABSTRACT

A test kit is used in an agglutination immunoassay to determine a multivalent immune species, such as Streptococcus A antigen, in a biological sample. The method includes contacting an aqueous solution of the species with an agglutination indicator reagent having receptor molecules reactive with the species to form an agglutinate of the reaction product of species and receptor. These receptor molecules are bound to polymeric particles which contain tracer molecules. The resulting agglutinate is captured on a microporous membrane which has an average pore size which is at least five times greater than the average diameter of the polymeric particles. Unagglutinated residual materials are washed through the membrane using a wash solution. This solution has a pH of from about 5 to about 10 and an ionic strength of at least about 0.25. Tracer is then determined either in the agglutinate or in the residual materials. The test kit includes the agglutination indicator reagent, the wash solution, and optionally an extraction composition.

21 Claims, 1 Drawing Sheet

AGGLUTINATION IMMUNOASSAY AND KIT FOR DETERMINATION OF A MULTIVALENT IMMUNE SPECIES USING A BUFFERED SALT WASH SOLUTION

FIELD OF THE INVENTION

The present invention relates to a method for the determination of a multivalent immune species, such as Streptococcus A, present in a biological sample. It also relates to a test kit useful in carrying out this method.

BACKGROUND OF THE INVENTION

The antigen-antibody reaction is the basis for all immunological test methods. Certain proteins known as antibodies are produced by mammals in response to the presence of an antigen, that is a foreign substance, which can be another protein or a carbohydrate. This normal body response to a foreign substance has led to the development of a number of techniques which are used to diagnose various diseases, disorders and physiological conditions. In a general sense, the component of the antibody-antigen reaction to be detected is defined herein as the immune species while the other corresponding component is considered the receptor.

In vitro tests for the presence of a suspected protein, antigen or antibody in a biological sample are carried out by adding the immunological counterpart to the biological sample. If the suspected substance is present, the resulting antigen-antibody reaction can be demonstrated by precipitation of the antigen-antibody complex. This reaction complex is generally difficult to detect visually. For this reason, either antibodies or antigens are often bound to insoluble particles, for example polymer latex particles, so that when the complex is formed, it is readily detectable from the resulting agglutination either by observing the presence of clumping or a detectable tracer associated with the particles. Agglutination then is characterized by the clumping of particles from a suspension of particles. Further details of known agglutination methods are provided in U.S. Pat No. 4,419,453 (issued Dec. 6, 1983 to Dorman et al) and U.S. Pat. No. 4,459,361 (issued July 10, 1984 to Gefter).

Of the several groups of Streptococci, group A Streptococcus (*S. pyogenes*) is primarily responsible for causing pathological conditions in humans, such as B-hemolytic pneumonia, scarlet fever, rheumatic fever, cardiac sequelae, glomerulonephritis, septic sore throat and puerperal sepsis. Because of the serious nature of infections potentially caused by Streptococcus A, it is important to diagnose its presence in an early stage of infection so that an appropriate course of treatment may be selected. Early tests for detection required culturing a biological sample for long periods of time, usually at least 18 and up to 48 hours. In most cases, such lengthy tests delay treatment making them undesirable.

More recent tests for Streptococcus A have been described which are allegedly quicker than the culturing techniques. U.S. Pat. No. 4,618,576 (issued Oct. 21, 1986 to Rosenstein et al) describes an agglutination test using certain enzymes to extract the antigen directly from the swab used to obtain a specimen from the throat. A kit comprising an applicator means for collecting the specimen, an extraction reagent containing the enzymes and suitable indicator reagents is also described. The described method comprises placing the extracted antigen in the wells of a sample plate along with latex particles coated with antibodies. After agitating the wells mechanically to facilitate antigen-antibody reaction, any agglutination is observed in the mixture in the wells. This method is disadvantageous because the agglutinate is not readily observable except with a microscope, and requires extraction enzymes prepared from a bacterium which must be cultured.

Other agglutination assays using various latex particles and coloring techniques for observing the agglutinate are described in E.P. Publications No. 150,567 and No. 174,195. U.S. Pat. No. 4,552,839 (issued Nov. 12, 1985 to Gould et al) describes an agglutination assay carried out by concentrating particles in a small area on a solid surface. The concentrated particles can have antibodies or label attached thereto to aid in detection of the analyte, that is, the antigen. The conditions of the assay are chosen to adjust the reaction of beads to each other. For example, the ionic strength of the aqueous medium is adjusted based on the natural charge of the particles in order to maximize agglutination. Generally, the ionic strength is varied from about 0.0001 to about 0.1. Once the agglutinate is formed and concentration on a bibulous material (for example, filter paper) is effected, a phosphate buffered saline wash containing a surfactant is applied to aid in wicking and separating unbound materials from bound materials (Col. 6, lines 50-55).

Current agglutination assays for a number of multivalent immune species [for example, Streptococcus A, human chorionic gonadotropin (hCG), Chlamydia, Gonorrhea, herpes, HIV, or human immunodeficiency viruses (formerly known as LAV or HTLV viruses) and others] are limited in usefulness in several respects. They are generally difficult to interpret, non-quantitative, subject to interferences and often insensitive. In order to improve the sensitivity and accuracy of agglutination assays for multivalent immune species carried out using antibody-bound particles, it has been found that a means is needed for keeping agglutinated materials from breaking apart and, at the same time, effectively separating agglutinated and unagglutinated materials.

SUMMARY OF THE INVENTION

The problems observed with known agglutination assays have been solved with an agglutination method for the determination of a multivalent immune species comprising:

(a) contacting an aqueous liquid containing the species in free form with a reagent comprising water-insoluble particles having tracer molecules associated therewith and receptor molecules reactive with the species bound to the surface thereof, so as to form an agglutinate of the reaction product of the species and the receptor molecules, (b) simultaneously or subsequent to contacting step (a), contacting the agglutinate with a microporous water-insoluble membrane having an average pore size which is at least 5 times greater than the average diameter of the water-insoluble particles, (c) washing unagglutinated residual materials through the membrane while leaving the agglutinate thereon, the washing accomplished with a wash solution having a pH of from about 5 to about 10 and an ionic strength of at least about 0.25, and (d) determining the amount of tracer either in the agglutinate remaining on the membrane or the residual materials.

In addition, the present invention provides a test kit for the determination of a multivalent immune species comprising:

an agglutination indicator reagent comprising water-insoluble particles having tracer molecules associated therewith and receptor molecules reactive with the species bound to the surface thereof, and a wash solution having a pH of from about 5 to about 10 and an ionic strength of at least about 0.25.

The present invention provides an agglutination assay which is highly accurate, easy to read, rapid and sensitive to the presence of the multivalent immune species, such as Streptococcus A, in an aqueous liquid such as a biological sample. This assay is quantitative, not merely qualitative. These advantages are achieved by carrying out the assay on a microporous membrane which has an average pore size which is at least five times greater than the average diameter of the water-insoluble particles carrying the species receptor. The particles readily agglutinate when the receptor and species react. It was found unexpectedly that the agglutinate remains on the membrane despite the relatively large pore size because a particular wash solution is used for washing unagglutinated residual materials from the agglutinate residing on a microporous membrane. The wash solution has a pH of from about 5 to about 10 and an ionic strength of at least about 0.25, as described in more detail below. Because of the relatively high ionic strength of the wash solution, the agglutinate holds together very well when unagglutinated residual materials are washed away. The result is effective separation and a more accurate, quantitative assay.

DETAILED DESCRIPTION OF THE INVENTION

The present invention provides a diagnostic test for a multivalent immune species which can be performed in a very short time, that is less than about 10 minutes, and without the use of complicated equipment. This permits the test to be performed in a doctor's office and enables the doctor to determine a course of treatment based upon the results of the test the same day. The test detects the presence of the species, such as Streptococcus A antigen, Clamydia or Gonorrhea antigen, or hCG in a biological sample, such as a swab specimen from the throat, urine speciment or sample of another aqueous liquid. Such biological samples can be tested with or without pretreatment (for example, filtration) to remove unwanted debris or interferents.

Figure 2:
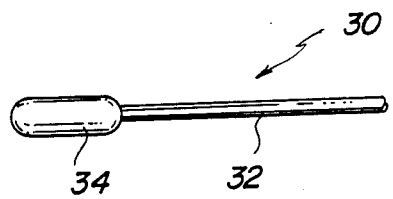
FIG. 2 is a plain view of a representative applicator means which can be included in the kit of this invention.

In accordance with this invention, a test kit provides the materials and reagents needed for carrying out the method of the invention. This kit generally includes (1) an agglutination indicator reagent comprising receptor molecules for the multivalent immune species bound to water-insoluble particles having tracer molecules associated therewith and (2) a wash solution having the properties noted herein. Optionally and preferably, the kit also includes a composition for extracting the species from a biological specimen if the species is not already in free form. Also optionally, the kit can comprise a neutralizing solution to neutralize the extraction composition after extraction has occurred or a suitable applicator means for collecting the biological specimen. An applicator means usually includes an applicator stick and a fibrous swab at one end thereof. Useful applicator means for Streptococcus A tests are known in the art and include those described, for example, in U.S. Pat. No. 4,618,576, noted above. A representative applicator means 30 is shown in FIG. 2 to have an applicator stick 32 with a fibrous swab 34 at one end thereof. All of these kit components are described in more detail below.

The method of this invention can be used to detect and quantify any of a wide variety of multivalent immune species. Such species are generally antigens which have at least two sites for complexing with the corresponding receptor, that is, corresponding antibodies. Alternatively, the multivalent species to be detected can be an antibody which has at least two complexing sites reactive with the corresponding antigen or an anti-antibody. Multivalent immune species which can be detected with this invention include, but are not limited to, Streptococcus A antigen, antigens from chlamydial and gonoccocal organisms, HIV (human immunodeficiency viruses) or antibodies, human chorionic gonadotropin (hCG), leutinizing hormone (LH), herpes viruses, drugs, antibiotics, and other hormonal, bacterial or viral antigens and antibodies. The species can be detected in free form which means that it is readily accessible to reactive receptor molecules. In some instances, the species must be extracted from the organism or virus found in the biological specimen. In other instances, the species is already in free form and requires no extraction procedures prior to the assay. Extraction procedures for a given species are known to one skilled in the art. Exemplary extraction procedures for Streptococcus A antigen are described below.

Preferably, the invention is used to detect Streptococcus A antigen as is demonstrated in the following embodiment and in Example 1 below. This embodiment of the invention relating to Streptococcus A antigen is presented for illustrative purposes, but it will be understood that the scope of the invention is not so limited. A biological sample suspected of containing the antigen can be collected from a patient in any suitable manner. However, generally an applicator means is used to collect a biological sample by contacting the area of suspected infection with the applicator swab thereby collecting cells of Streptococcus A organisms if they are present. Subsequently, the antigens are extracted from the organisms in a suitable manner. A preferred extraction procedure includes dipping the swab in a suitable extraction composition containing one or more reagents which singly or in combination cause release of the Streptococcus A antigen from the organism, specimen cells and other debris in the sample.

Useful extraction compositions known in the art include a mixture of nitrite salt and glacial acetic acid, as described in E.P. Publication 150,567, noted above. Another extraction procedure involves the use of enzymes derived from the bacterium Streptomyces albus as described in U.S. Pat. No. 4,618,576, noted above. A preferred extraction composition is a mixture of a nitrite salt (for example, sodium nitrite or potassium nitrite) with an organic acid (for example, malonic or citric acid). When used in the method of this invention, these two reagents of the composition combine to form a solution of nitrous acid which is a strong extraction reagent.

Extraction can be accompanied by incubation for a short period of time if desired. Centrifugation can also be used to remove extraneous material. After extraction, the medium containing the extracted antigen can be neutralized if necessary to bring the medium pH to that appropriate for antigen-antibody reaction. For example, when extraction is carried out with citric acid and a nitrite salt, the pH is lowered below that optimally desired for reaction. In that case, the medium is neutralized with a suitable buffer. Such optional steps are noted, for example, by Slifkin et al, *J. Clin. Microbiol.* 15(1), pp. 187–189, 1982.

The presence of a multivalent immune species in free form, for example, Streptococcus A antigen, is detected by an agglutination indicator reagent which comprises water-insoluble particles having tracer molecules associated therewith and receptor molecules (for example, antibodies to Streptococcus A antigen) reactive with the species bound in a suitable manner to the surface of the particles. Reaction (or binding) between immune species and receptor then results in a linking together of the particles so that they agglutinate and precipitate out of suspension.

Suitable particles useful in the indicator reagent can be natural or synthetic particles which are water-insoluble and capable of having a suitable number of tracer molecules associated therewith in some manner. Examples of useful particles include ferritin crystals, agarose particles, glass beads, polymeric particles, such as latex particles, and others known in the art. The following references describe representative useful particles: U.S. Pat. No. 3,700,609 (issued Oct. 24, 1972 to Tregear et al), U.S. Pat No. 3,853,987 (issued Dec. 10, 1974 to Dreyer), U.S. Pat. No. 4,108,972 (issued Aug. 22, 1978 to Dreyer), U.S. Pat No. 4,401,765 (issued Aug. 30, 1983 to Craig et al), U.S. Pat. No. 4,419,453 issued Dec. 6, 1983 to Dorman et al), U.S. Pat. No. 4,459,361 (issued July 10, 1984 to Gefter), U.S. Pat. No. 4,478,946 (issued Oct. 23, 1984 to Van der Merwe) and U.S. Pat. No. 4,591,571 (issued May 27, 1986 to Kuboyama et al). The particles useful in this invention are generally quite small, that is less than about 1 micrometer in diameter. Preferably, they have an average diameter of from about 0.1 to about 0.7, and most preferably from about 0.3 to about 0.5, micrometer.

Particularly useful particles are polymeric latex particles, and more preferably they are what are known in the art as core-shell polymeric latex particles. A wide variety of monomers can be used in the preparation of such particles as long as the particles are water-insoluble. A worker skilled in the polymer chemistry art would be able to design and prepare suitable latex particles. Preferred core-shell polymeric latex particles in the practice of this invention are described in the examples below. These particles have a core composed of homo- or copolymers of styrene, and a shell composed of homo- or copolymers of chloromethylstyrene.

The particles useful in the practice of this invention have sufficient tracer molecules associated therewith in order to allow quantitative determination of the species from the amount of tracer seen in either the agglutinate or in the unagglutinated residual materials. The tracer molecules can be suitably attached to the outer surface of the particles, or preferably, distributed within the particles. Any tracer material which allows detection of the agglutinate can be used. If ferritin crystals are used as the particles, the tracer molecules are molecules of iron inherently in those crystals. Other natural or synthetic particles can have, as tracers: radioisotopes, colorimetric dyes, fluorescent compounds, chemiluminescent compounds, phosphorescent compounds and other detectable materials known in the art. Preferably, the tracer is a radioisotope, colorimetric dye or fluorescent compound (for example, dye or rare earth chelate). A worker skilled in the art would be able to combine an appropriate tracer with the particular particle used.

In one embodiment, the tracer can be a fluorescent rare earth chelate such as a europium chelate, as described for example, in U.S. Pat No. 4,259,313 (issued Mar. 31, 1981 to Frank et al). In another and preferred embodiment, the tracer is a colorimetric dye which is readily detected in the agglutinate. Useful dyes are known in the art. Some dyes can be incorporated into the particles when the particles are prepared. Alternatively, the dyes are imbibed into preformed particles in such a manner that they do not leach out.

The tracer can be distributed within the particles in any suitable manner. For example, the tracer can be uniformly distributed therein as shown for example in U.S. Pat. No 3,853,987 (noted above). Preferably, the tracer molecules are located in a restricted area of the particles, for example, near the surface or predominantly in the interior thereof. In the preferred core-shell particles, the tracer can be in either the core or shell, but most preferably, it is substantially in the core of the particles. In other words, very little (for example, less than 5% by weight) of the dye is in the shell portion of the particles.

Receptor molecules (for example, antibodies) reactive to the immune species to be detected, such as Streptococcus A antigen, are bound to the outer surfaces of the particles in a suitable manner, for example by adsorption or covalent attachment. Attachment can be achieved using known techniques, as described for example in the references cited above. Covalent attachment is preferred as the receptor molecules are less likely to be removed from the particles. When covalently attached, the receptor molecules can be bound directly to the particles or through suitable linking groups. When the receptor molecules are antibodies, either monoclonal or polyclonal antibodies can be used, but monoclonal antibodies are preferred. Antibodies can be obtained commercially or prepared using known techniques. Polyclonals, for example, are generally prepared by injecting antigen into suitable mammals which then generate the antibodies which can be removed for use. Monoclonals are obtained using conventional hybridoma technology. When the receptor molecules are antigens, the desired antigen molecules can be obtained using known procedures for isolating the molecules from suitable biological sources. For example, HIV antigens can be obtained from the sera of patients infected with the virus.

Simultaneously or subsequent to contact of extracted multivalent immune species with receptor molecules to form the agglutinate, the agglutinate is also contacted with a microporous water-insoluble membrane. In one embodiment, the agglutinate can be formed in a separate container and then brought into contact with the membrane. Alternatively and preferably, the agglutinate is formed in the presence of the membrane. This membrane (described in detail below) can be simply a filter means held by hand through which unagglutinated materials are filtered. Preferably, however, it is mounted in a test device in which the assay is carried out. Such a test device is also described below.

Any microporous water-insoluble membrane can be used as long as it is inert to the materials used in the assay, and has the desired porosity which will allow fluids and nonagglutinated materials to pass through but which will retain agglutinated materials. In other words, the membrane pores must be large enough to allow passage of the indicator reagent, antigen and unagglutinated particles, but not large enough to allow agglutinated particles to pass through. More particularly, the average pore size of the membrane must be at least five times the average diameter of the water-insoluble particles described above. Preferably, the average pore size is from about 6 to about 15 times the average particle diameter. Useful membranes include polymeric materials which are commercially available from various sources, such as Pall Corp (Glen Cove, New York). One useful membrane is a nylon 66 microporous membrane manufactured and marketed by that company as BIODYNE or ULTIPOR.

A suitable incubation period can be used to optimize agglutination, if desired, before or during contact with the membrane. After that period, unagglutinated residual materials are washed through the membrane while leaving the agglutinate thereon. A critical feature of this invention is carrying out this wash step with a wash solution which has a pH of from about 5 to about 10 and which contains an ionic compound as described below. Preferably, the solution is buffered to a pH of from about 6 to about 9.

Any suitable organic or inorganic buffer can be used in the wash solution as long as it provides the desired pH. Useful buffers include glycine, tricine, 2-(N-morpholino)ethanesulfonic acid, 3-(N-morpholino)propanesulfonic acid and others known to one skilled in the art.

The wash solution contains one or more ionic compounds which are present at a concentration sufficient to give the solution an ionic strength of at least about 0.25. Preferably, the solution ionic strength is from about 0.5 to about 3. Ionic compounds can be used to supply the desired ionic strength. Such compounds are those which are ionized in aqueous solution to a high degree. Such compounds can be monovalent salts such as sodium chloride, potassium chloride and others known to one skilled in the art. Sodium chloride is preferred. Alternatively, the ionic compound can be a compound which is sufficiently ionized at the pH of the wash solution, but which may not be completely ionized under all conditions. Examples of such compounds include buffers, such as tricine, glycine, sodium glycinate, sodium tricine, 3-(N-morpholino)propanesulfonic acid, sodium salt and others apparent to one skilled in the art.

Once the unagglutinated residual materials have been washed through the membrane, the amount of multivalent immune species in either the agglutinate or residual materials can generally be determined with the unaided eye if the tracer is a readily viewable colorimetric dye. Otherwise, standard colorimetric detection equipment can be used. Other types of tracers, for example, radioisotopes, fluorescent dyes, phosphorescent dyes, and the like, require suitable detection equipment.

In a preferred embodiment of this invention, a method for detecting Streptococcus A comprises:
(i) providing an applicator including an applicator stick and a fibrous swab and collecting a biological sample with the swab,
(ii) providing an extraction composition comprising sodium nitrite and citric acid for effecting release of Streptococcus a antigen from the swab, dipping the swab in the extraction composition and incubating the swab within the extraction composition for a period of time sufficient to release antigen from said swab,
(iii) neutralizing the solution of extracted antigen,
(iv) contacting the neutralizing solution of extracted antigen with an agglutination indicator reagent comprising water-insoluble, polymeric core-shell latex particles containing tracer molecules substantially in the particle cores and comprising antibodies reactive with the antigen bound to the surface thereof, so as to form an agglutinate of the reaction product of the antigen and the antibodies, the contacting being carried out in the presence of a microporous water-insoluble membrane mounted in a disposable test device, the membrane having an average pore size which is at least five times the average diameter of the water-insoluble particles described above,
(v) washing unagglutinated residual materials through the membrane while leaving the agglutinate thereon, the washing accomplished with a wash solution having a pH of from about 6 to about 9 and an ionic strength of from about 0.5 to about 3, and
(vi) determining the amount of tracer in the agglutinate remaining on the membrane.

Figure 1:
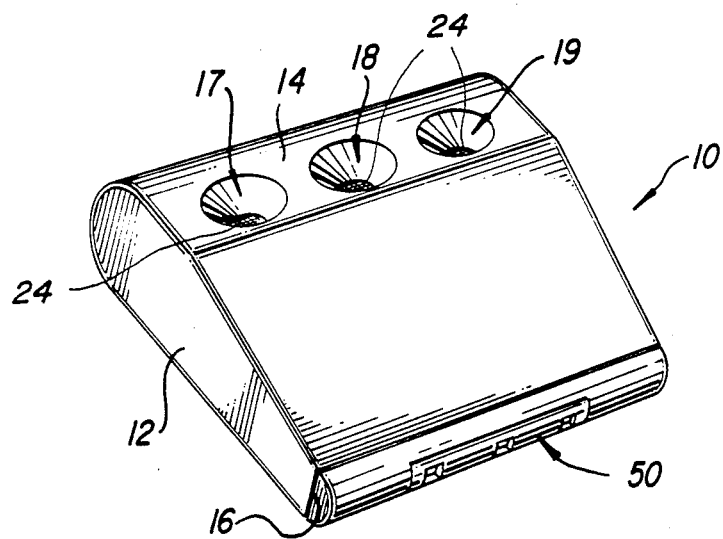
FIG. 1 is a perspective illustration of a representative disposable test device which can be included in the kit of this invention.

While the present invention is not so limited, the assay for a multivalent immune species can be carried out using a suitable test device which comprises the microporous membrane described herein. Such a device can have one or more sample wells into which extracted antigen is deposited for reaction with the agglutination indicator reagent. This reagent can be added to the device during the assay, or incorporated therein at the time of manufacture. Once the agglutinate is formed, the unagglutinated residual materials can be washed through the membrane with the wash solution into a separate compartment below the membrane. An example of such a test device is described and claimed in copending and commonly assigned U.S. Ser. No. 019,810 entitled Disposable Container Configured To Produce Uniform Signal and filed on the same date herewith by Hinckley. A representative disposable test device 10, FIG. 1, has frame 12 having top surface 14 and front edge 16. Mounted on edge 16 is a slide valve 50 for prohibiting or allowing drainage of fluids from the three test wells 17, 18, and 19 located in top surface 14. At the bottom of each of test wells 17, 18 and 19 is mounted a microporous membrane 24 (partially obscured) through which unagglutinated materials flow while agglutinated materials are retained in an assay. Other variations of useful test devices would be within the purview of an ordinary worker skilled in the art.

In the examples which follow, illustrating the practice of this invention, the materials used were obtained as follows:
casein and human chorionic gonadotropin (hCG) from Sigma Chemical Co. (St. Louis, Missouri),
nylon 66 membranes from Pall Corp. (Glen Cove, New York),
Oil Red EGN dye from Aldrich Chemical Co. (Milwaukee, Wisconsin),
succinylated casein was prepared by reacting casein with an equal weight of succinic anhydride for four hours at 25° C., and then purifying the product by dialysis, monoclonal antibodies to the PI antigen of serogroup B of *Neisseria gonorrhea* were obtained using the F62 strain according to the procedure described by Schneider et al in *J. Immun. Meth.*, 54, pp. 101–105, 1982, monoclonal antibodies to Streptococcus A antigen were obtained from Streptococcus A vaccine according to the procedure described by McCarty et al, *J. Exp. Med.*, 102, 11, 1955, monoclonal antibodies to hCG were mouse IgG$_1$ antibodies produced by standard hybridoma technology and had affinities of about $10^9$ molar$^{-1}$, and the remainder either from Eastman Kodak Company (Rochester, New York, U.S.A.) or Cetus Corporation (Emeryville, California) or prepared using standard procedures and readily available starting materials.

EXAMPLE 1

Comparative Example for the Determination of Streptococcus A

This example demonstrates the practice of the present invention for the determination of Streptococcus A antigen. It also compares the practice of the present invention using a wash solution having a salt concentration of at least 0.25 molar (that is, at least 0.25 ionic strength to an assay outside the scope of this invention using a wash solution containing less than 0.25 molar salt (that is, less than 0.25 ionic strength).

Core-shell polymeric latex particles containing a red dye (Oil Red EGN) in the core were prepared by imbibing the dye into the particles that had been prepared using core/shell polymerization techniques. The core of the particles was composed of poly(styrene-co-2-acetoacetoxyethyl methacrylate) (70:30 weight ratio) while the shell was composed of poly(m,p-chloromethylsytrene). The average diameter of the particles was about 0.45 micrometer. Monoclonal antibodies to Streptococcus A antigen were immobilized on these particles as follows: to 0.6 ml of 50 mmolar borate buffer (pH 8.5) was added 0.1 mg of total protein comprised of a 10:1 mixture of anti-Strep A antibody (purchased as a 2.9 mg/ml solution in phosphate buffered saline solution, known in the art as PBS) and casein (10 mg/ml water). After mixing, 41.5 μl of a 5% suspension of the polymeric latex particles were added (to provide 0.3% solids) and the resulting solution was rotated (end-over-end) for 24 hours at 37° C. to effect covalent attachment of the antibody to the outer surfaces of the particles and the formation of an agglutination indicator reagent.

A solution of succinic anhydride (10 mg/ml dimethyl sulfoxide) was added to a suspension of the agglutination indicator reagent described above at a weight ratio of 1 part anhydride to 1 part total protein. The resulting suspension was mixed for four hours at 25° C., centrifuged for 5 minutes at 7000 rpm and the resulting pellet was resuspended in 0.1 molar glycine buffer (pH 8.5) to a concentration of 0.3% solids.

An isolate of Streptococcus A obtained from a local hospital was used in the assays of this example. Streptococcus A antigen was extracted from an isolate at 25° C. for 1 minute using a solution of equal volumes of sodium nitrite (8 molar) and citric acid (0.2 molar). The solution was then neutralized with an equal volume of 3-(N-morpholino)propane-sulfonic acid buffer (2 molar, pH 7.5) containing ethylenediaminetetraacetic acid (75 mmolar).

A nylon 66 microporous membrane (5 μm average pore size) was incorporated into a test well of a disposable test device like that described and claimed in U.S. Ser. No. 019,810 of Hinckley, noted above, and pretreated by washing with 100 μl of a 2% succinylated casein solution.

A mixture of sodium chloride (80 μl, 1 molar), the agglutination indicator reagent suspension described above (40 μl), and extracted antigen (80 μl) containing about $4.2 \times 10^5$ colony-forming units per ml was added to the test well of the test device containing the membrane, and incubated therein for two minutes at 25° C. The fluid was then allowed to drain into a compartment below the membrane, and the agglutinate on the membrane was washed with 150 μl of the wash fluids shown in Table I below. Control A was distilled water while Control B was a wash solution containing 0.025 molar sodium chloride (that is, 0.025 ionic strength).

After the washing step, the amount of dye in the agglutinate on the membrane was measured at 540 nm using reflectance measuring equipment. The Williams-Clapper transform (*J. Optical Soc. Am.*, 43, p. 595, 1953) was used to calculate transmission density values. The results of the measurements are shown in Table I below as $\Delta D_T$, difference between the dye formed from the test samples and background readings from controls containing no antigen. It can be seen from the data that the assays of the present invention using a high concentration of salt in the wash solution provided a readily observable agglutinate on the membrane. The Control A and B assays, however, in which little dye was observed, demonstrate that the lack of sufficient salt in the wash solution prohibits adequate retention of agglutinate on the membrane.

TABLE I

| Ionic Strength | | $\Delta D_T$ |
|---|---|---|
| 0 | (Control A) | 0.018 |
| 0.025 | (Control B) | 0.022 |
| 0.25 | | 0.148 |
| 0.5 | | 0.152 |
| 1.0 | | 0.170 |
| 3.0 | | 0.114 |

EXAMPLE 2

Determination of Gonorrhea

This example demonstrates the practice of the present invention for the determination of gonorrhea. The agglutination indicator reagent used in this example was composed of latex particles comprised of poly(styrene-co-m,p-chloromethylstyrene-co-2-hydroxyethyl acrylate) (76:23:1 weight ratio) into which had been imbibed 5%, by weight, of europium (III) (thenoyltrifluoroacetone)$_3$ along with trioctylphosphine oxide in the ratio of 1 part chelate to 2 parts oxide according to the procedures described in Belgian Pat. No. 843,647. The particles had an average diameter of about 0.45 micrometer.

Monoclonal antibodies to the PI antigen of the serogroup B of *Neisseria gonorrhea* (also known in the art as the PIB antigen) were immobilized on the particles described above as follows: to 1.3 ml of 50 mmolar borate buffer (pH 8.5) was added 0.15 ml of 1.08 mg/ml antibody solution in phosphate buffered saline (PBS) and 0.32 ml of a 1 mg/ml solution of casein in water.

After mixing, 41.5 μl of a 5% suspension of the latex particles described above were added, and the resulting solution was mixed at 37° C. for 24 hours. Succinic anhydride (0.174 ml of 10 mg/ml dimethyl sulfoxide solution) was added, and the resulting solution was mixed at 22° C. for four hours. This solution was then centrifuged for 10 minutes and the resulting pellet was resuspended in 0.1 molar glycine (pH 8.5) to give a mixture containing 0.3% solids of agglutination indicator reagent.

The PIB antigen was extracted from a specimen of Neisseria gonorrhea using a mixture of 1% ethanolamine and 10 mmolar ethylenediaminitetraacetic acid, followed by sonication and filtration.

A nylon 66 microporous membrane having an average pore size of 5 micrometers was pretreated by dipping it into a 2% casein solution. A mixture of sodium chloride (50 μl, 6 molar), antigen solution (50 μl) having a specific amount of antigen (nanogram) and the agglutination indicator solution described above (50 μl) was added to a test tube, incubated at 22° C. for 30 minutes, then filtered through the treated microporous membrane. The resulting agglutinate on the membrane was washed with 0.15 μl of 1 molar tricine (pH 8.6). The amount of agglutinate was determined by measuring the amount of fluorescence in the agglutinate using standard surface fluorescence measuring equipment (excitation, 342 nm and emission, 610 nm). A Control solution containing specific amounts of an extract of a different antigen (that is, the PI antigen of the serogroup A of Neisseria gonorrhea, or also known as the PIA antigen) was treated in the same manner in order to measure nonspecific interactions with the antibodies to the PIB antigen. Table II below shows the results of these tests. It is clear that the assay of this invention can be used to determine a desired antigen of a specific serogroup of gonorrhea.

TABLE II

| PIB Antigen Concentration (ng) | Relative Fluorescence | |
|---|---|---|
| | Test | Control |
| 100 | 107 | 32 |
| 10 | 332 | 120 |
| 1 | 248 | 73 |

EXAMPLE 3

Assay for Human Chorionic Gonadotropin

This example demonstrates the practice of the present invention for the determination of human chorionic gonadotropin (hCG).

Core/shell polymeric particles were imbibed with Oil Red EGN dye according to known procedures. The particle cores were composed of poly(styrene-co-2-acetoacetoxyethyl methacrylate) (85:15 weight ratio), and the particle shells were composed of poly(m,p-chloromethylstyrene-co-methacrylic acid) (99.8:0.2 weight ratio). The particles had an average diameter of about 0.32 micrometer.

Monoclonal antibodies to two different epitopic sites of hCG were immobilized on these particles as follows: to 0.6 ml of 50 mmolar borate buffer (pH 8.5) were added 0.1 mg of 10:1 mixture of hCG antibody (2.9 mg/ml phosphate buffered saline solution) and casein (10 mg/ml water). After mixing, 41.5 μl of a 5% suspension of the latex particles described above were added and the resulting suspension was rotated (end-over-end) for 24 hours at 37° C. to effect covalent attachment of the antibodies to the particles and formation of an agglutination indicator reagent.

A solution of succinic anhydride (10 mg/ml dimethyl sulfoxide) was added to a mixture of the agglutination indicator reagent at a weight ratio of 1 part anhydride to 1 part total protein, and the resulting mixture was mixed for 4 hours at 25° C., centrifuged for 5 minutes at 7000 rpm. The resulting pellet was resuspended in 0.1 molar glycine (pH 8.5) to a concetration of 0.3% solids.

Various amounts of hCG (milli I.U./ml) were added to phosphate buffered saline solutions (0.1 molar sodium phosphate and 0.15 sodium chloride) containing 0.5% bovine serum albumin. A nylon 66 microporous membrane having an average pore size of about 5 micrometers was incorporated into a test well of a disposable test device similar to that described in Example 1 above. This membrane was washed with 2 drops of a 1% aqueous solution of succinylated casein. The hCG concentration in milli I.U. is defined as 5000 milli I.U. being equivalent to 1 microgram of purified hCG.

A mixture of 60 μl of 4 molar sodium chloride, 1 molar tricine buffer (pH 8.6), 60 μl of suspension of the agglutination indicator reagent described above and 240 μl of the hCG solutions described above was added to test tubes, gently mixed and allowed to incubate at 25° C. for 10 minutes. A portion of each solution (300 μl) was added to the test well containing the membrane and allowed to flow through the membrane. Agglutinate formed on the membrane did not flow through, however. It was washed with 300 μl of a 1 molar sodium chloride solution, and the amount of dye in the agglutinate was measured at 540 nm as described in Example 1. The results of these measurements are shown in Table III below as transmission density ($D_T$). It indicates that the assay of this invention can be used to determine hCG.

TABLE III

| hCG Antigen (milli I.U./ml) | $D_T$ |
|---|---|
| 0 | 0.043 |
| 500 | 0.047 |
| 1000 | 0.133 |

The invention has been described in detail with particular reference to preferred embodiments thereof, but it will be understood that variations and modifications can be effected within the spirit and scope of the invention.

We claim:

1. An agglutination method for the determination of a multivalent immune species comprising:
   (a) contacting an aqueous liquid containing said species in free form with a reagent comprising water-insoluble particles having tracer molecules associated therewith and receptor molecules reactive with said species bound to a surface thereof, so as to form an agglutinate of a reaction product of said species and said receptor molecules,
   (b) simultaneously or subsequent to said contacting step (a), contacting said agglutinate with a microporous water-insoluble membrane having an average pore size which is at least 5 times greater than the average diameter of said water-insoluble particles,
   (c) washing unagglutinated residual materials through said membrane while leaving said agglutinate thereon, said washing accomplished with a wash solution having a pH of from about 5 to about 10 and an ionic strength of at least about 0.25, and (d) determining the amount of tracer molecules either in said agglutinate remaining on said membrane or said residual materials.

2. The method of claim 1 wherein said wash solution has an ionic strength of from about 0.5 to about 3.

3. The method of claim 1 wherein said wash solution has a pH of from about 6 to about 9.

4. The method of claim 1 wherein said species is extracted from a biological sample with an extraction composition prior to said contacting step (a).

5. The method of claim 1 wherein said contacting step (a) is carried out simultaneously with contact with said microporous membrane.

6. The method of claim 1 for the determination of an antigen wherein said receptor molecules are antibodies for said antigen which are covalently bound to said water-insoluble particles.

7. The method of claim 1 for the determination of antibodies wherein said receptor molecules are antigen molecules reactive with said antibodies.

8. The method of claim 1 wherein said water-insoluble particles contain molecules of a colorimetric dye as tracer molecules.

9. The method of claim 1 wherein said tracer molecules are rare earth chelate molecules.

10. The method of claim 1 wherein said tracer molecules are determined in said agglutinate on said membrane.

11. The method of claim 1 wherein said water-insoluble particles have an average diameter of less than about 1 micrometer.

12. The method of claim 11 carried out using a disposable test device containing said microporous membrane.

13. An agglutination method for the determination of Streptococcus A in a biological sample comprising:

(a) extracting Streptococcus A antigen from said sample with an extraction composition, (b) contacting said extracted antigen with a reagent comprising water-insoluble, polymeric latex particles having tracer molecules distributed therein and antibodies reactive with said extracted antigen covalently bound to a surface thereof, so as to form an agglutinate of a reaction product of said antigen and said antibodies, said contacting being carried out in an aqueous mixture in the presence of a microporous water-insoluble membrane having an average pore size which is at least five times greater than the average diameter of said water-insoluble particles, (c) washing unagglutinated residual materials through said membrane while leaving said agglutinate thereon, said washing accomplished with a wash solution having a pH of from about 6 to about 9 and an ionic strength from about 0.25 to about 3, and (d) determining an amount of said tracer molecules in said agglutinate remaining on said membrane.

14. The method of claim 13 wherein said extraction is carried out with an extraction composition comprising a nitrite salt and citric acid.

15. The method of claim 13 wherein said polymeric latex particles are core-shell latex particles containing substantially all of said tracer molecules in a particle core and having an average diameter of from about 0.1 to about 0.7 micrometer.

16. The method of claim 13 wherein said tracer molecules are colorimetric dye molecules.

17. A method for detecting Streptococcus A comprising:

(i) providing an applicator including an applicator stick and a fibrous swab and collecting a biological sample with said swab, (ii) providing an extraction composition comprising sodium nitrite and citric acid for effecting release of Streptococcus A antigen from said swab, dipping said swab in said extraction composition and incubating said swab within said extraction composition for a period of time sufficient to release antigen from said swab, (iii) neutralizing the solution of said extracted antigen, (iv) contacting said neutralized solution of said extracted antigen with an agglutination indicator reagent comprising water-insoluble, polymeric core-shell latex particles having an average diameter of from about 0.1 to about 0.7 micrometer, and having molecules of a colorimetric dye distributed substantially in particle cores and comprising antibodies reactive with said antigen bound to the surface thereof, so as to form an agglutinate of a reaction product of said antigen and said antibodies, said contacting being carried out in the presence of a microporous water-insoluble membrane mounted in a disposable test device, said membrane having an average pore size which is at least 5 times greater than an average diameter of said water-insoluble particles (v) washing unagglutinated residual materials through said membrane while leaving said agglutinate thereon, said washing accomplished with an aqueous wash solution having a pH of from about 6 to about 9 and an ionic strength of from about 0.5 to about 3, and (vi) determining the amount of colorimetric dye molecules in said agglutinate remaining on said membrane.

18. The method of claim 17 wherein said aqueous wash solution comprises sodium chloride.

19. A test kit for the determination of a multivalent immune species comprising:

an agglutination indicator reagent comprising water-insoluble particles having tracer molecules associated therewith and receptor molecules reactive with said species bound to the surface thereof, and a wash solution having a pH of from about 5 to about 10 and an ionic strength of at least about 0.25.

20. The test kit of claim 19 for the determination of Streptococcus A antigen further comprising:

an applicator means for collecting a biological sample suspected of containing Streptococcus A, said applicator means including an applicator stick and a swab at one end thereof that collects said sample, and an extraction composition for extracting Streptococcus A antigen from Streptococcus A present in said sample.

21. The test kit of claim 19 further comprising a disposable test device comprising a microporous water-soluble membrane mounted in a test well of said test device, said membrane having an average pore size which is at least five times greater than the average diameter of said water-insoluble particles.

* * * * *